(12) United States Patent
Wenchell

(10) Patent No.: US 11,051,805 B2
(45) Date of Patent: Jul. 6, 2021

(54) SYSTEM AND METHOD OF USING SIMULATION RELOAD TO OPTIMIZE STAPLE FORMATION

(71) Applicant: Covidien LP, Mansfield, MA (US)

(72) Inventor: Thomas Wenchell, Durham, CT (US)

(73) Assignee: COVIDIEN LP, Mansfield, MA (US)

( * ) Notice: Subject to any disclaimer, the term of this patent is extended or adjusted under 35 U.S.C. 154(b) by 1426 days.

(21) Appl. No.: 15/179,293

(22) Filed: Jun. 10, 2016

(65) Prior Publication Data

US 2016/0278767 A1  Sep. 29, 2016

Related U.S. Application Data

(62) Division of application No. 13/633,213, filed on Oct. 2, 2012, now Pat. No. 9,364,231.

(Continued)

(51) Int. Cl.
*A61B 17/068* (2006.01)
*A61B 90/00* (2016.01)
(Continued)

(52) U.S. Cl.
CPC ...... *A61B 17/068* (2013.01); *A61B 17/07207* (2013.01); *A61B 17/105* (2013.01); *A61B 90/06* (2016.02); *A61B 2017/00017* (2013.01); *A61B 2017/00022* (2013.01); *A61B 2017/00398* (2013.01); *A61B 2017/00464* (2013.01);
(Continued)

(58) Field of Classification Search
CPC .... A61B 17/07207; A61B 2017/00464; A61B 2017/0017; A61B 2019/464
See application file for complete search history.

(56) References Cited

U.S. PATENT DOCUMENTS 2,777,340 A   1/1957  Hettwer et al.
2,957,353 A  10/1960  Babacz
(Continued)

FOREIGN PATENT DOCUMENTS

CA   2451558 A1   1/2003
CN   1547454 A   11/2004
(Continued)

OTHER PUBLICATIONS

Extended European Search Report corresponding to counterpart International Application No. EP 14 18 4882.0 dated May 12, 2015.
(Continued)

*Primary Examiner* — Andrew M Tecco

(57) ABSTRACT

The present disclosure is directed to a testing systems and methods for testing a powered surgical instrument. The powered surgical instrument includes a processor configured to control operation of the powered surgical instrument, a memory configured to store a tissue compression program, a reload configured to clamp tissue, a motor configured to control the reload to apply a compressive force to the tissue by the reload, and at least one sensor configured to measure a current draw on the motor. The processor executes the simulation program to measure the current draw on the motor through a nominal thickness firing and the measured current draw is used to adjust the tissue compression program.

9 Claims, 5 Drawing Sheets

Related U.S. Application Data

(60) Provisional application No. 61/551,956, filed on Oct. 27, 2011.

(51) Int. Cl.
*A61B 17/072* (2006.01)
*A61B 17/10* (2006.01)
*A61B 17/00* (2006.01)
*A61B 17/29* (2006.01)
*A61B 17/32* (2006.01)

(52) U.S. Cl.
CPC ........... A61B 2017/00473 (2013.01); A61B 2017/00725 (2013.01); A61B 2017/00734 (2013.01); A61B 2017/2927 (2013.01); A61B 2017/320052 (2013.01); A61B 2090/065 (2016.02)

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 3,866,510 A | 2/1975 | Eibes et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,886,246 A | 3/1999 | Bareggi et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |

(56) References Cited

U.S. PATENT DOCUMENTS

| | | |
|---|---|---|
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,063 B2 * | 4/2011 | Zemlok ............ A61B 17/07207 227/176.1 |
| 7,922,719 B2 | 4/2011 | Ralph et al. |
| 7,947,034 B2 | 5/2011 | Whitman |
| 7,950,560 B2 | 5/2011 | Zemlok et al. |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,062,236 B2 * | 11/2011 | Soltz ............ A61B 17/068 600/587 |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,025 B2 * | 10/2013 | Soltz ............ A61B 17/068 600/587 |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,900,164 B2 * | 12/2014 | Soltz ............ A61B 17/068 600/587 |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,217 B2 * | 3/2015 | Soltz ............ A61B 17/068 600/587 |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |

(56) References Cited

U.S. PATENT DOCUMENTS

| | | | |
|---|---|---|---|
| 9,023,014 B2 | 5/2015 | Chowaniec et al. | |
| 9,033,868 B2 | 5/2015 | Whitman et al. | |
| 9,055,943 B2 | 6/2015 | Zemlok et al. | |
| 9,064,653 B2 | 6/2015 | Prest et al. | |
| 9,072,515 B2 | 7/2015 | Hall et al. | |
| 9,113,847 B2 | 8/2015 | Whitman et al. | |
| 9,113,875 B2 | 8/2015 | Viola et al. | |
| 9,113,876 B2 | 8/2015 | Zemlok et al. | |
| 9,113,899 B2 | 8/2015 | Garrison et al. | |
| 9,216,013 B2 | 12/2015 | Scirica et al. | |
| 9,241,712 B2 | 1/2016 | Zemlok et al. | |
| 9,282,961 B2 | 3/2016 | Whitman et al. | |
| 9,282,963 B2 | 3/2016 | Bryant | |
| 9,295,522 B2 | 3/2016 | Kostrzewski | |
| 9,307,986 B2 | 4/2016 | Hall et al. | |
| 9,364,231 B2 | 6/2016 | Wenchell | |
| 2001/0007074 A1 | 7/2001 | Strobel et al. | |
| 2001/0031975 A1 | 10/2001 | Whitman et al. | |
| 2002/0049454 A1 | 4/2002 | Whitman et al. | |
| 2002/0165541 A1 | 11/2002 | Whitman | |
| 2003/0009441 A1 | 1/2003 | Holsten et al. | |
| 2003/0038938 A1 | 2/2003 | Jung | |
| 2003/0105478 A1* | 6/2003 | Whitman | A61B 17/07207 606/167 |
| 2003/0125717 A1* | 7/2003 | Whitman | A61B 17/068 606/1 |
| 2003/0165794 A1 | 9/2003 | Matoba | |
| 2004/0034369 A1 | 2/2004 | Sauer et al. | |
| 2004/0094597 A1* | 5/2004 | Whitman | A61B 17/07207 227/180.1 |
| 2004/0111012 A1 | 6/2004 | Whitman | |
| 2004/0111081 A1* | 6/2004 | Whitman | A61B 10/0233 606/1 |
| 2004/0133189 A1 | 7/2004 | Sakurai | |
| 2004/0153124 A1 | 8/2004 | Whitman | |
| 2004/0176751 A1 | 9/2004 | Weitzner et al. | |
| 2004/0193146 A1 | 9/2004 | Lee et al. | |
| 2005/0125027 A1 | 6/2005 | Knodel et al. | |
| 2005/0131442 A1 | 6/2005 | Yachia et al. | |
| 2006/0142656 A1 | 6/2006 | Malackowski et al. | |
| 2006/0142740 A1 | 6/2006 | Sherman et al. | |
| 2006/0142744 A1 | 6/2006 | Boutoussov | |
| 2006/0259073 A1 | 11/2006 | Miyamoto et al. | |
| 2006/0278680 A1 | 12/2006 | Viola et al. | |
| 2006/0284730 A1 | 12/2006 | Schmid et al. | |
| 2007/0023476 A1 | 2/2007 | Whitman et al. | |
| 2007/0023477 A1 | 2/2007 | Whitman et al. | |
| 2007/0029363 A1 | 2/2007 | Popov | |
| 2007/0084897 A1 | 4/2007 | Shelton et al. | |
| 2007/0102472 A1 | 5/2007 | Shelton | |
| 2007/0152014 A1 | 7/2007 | Gillum | |
| 2007/0175947 A1 | 8/2007 | Ortiz et al. | |
| 2007/0175949 A1 | 8/2007 | Shelton et al. | |
| 2007/0175950 A1 | 8/2007 | Shelton et al. | |
| 2007/0175951 A1 | 8/2007 | Shelton et al. | |
| 2007/0175955 A1 | 8/2007 | Shelton et al. | |
| 2007/0175961 A1 | 8/2007 | Shelton et al. | |
| 2007/0179408 A1* | 8/2007 | Soltz | A61B 17/068 600/587 |
| 2007/0270784 A1 | 11/2007 | Smith et al. | |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0058801 A1 | 3/2008 | Taylor et al. | |
| 2008/0109012 A1 | 5/2008 | Falco et al. | |
| 2008/0110958 A1 | 5/2008 | McKenna et al. | |
| 2008/0147089 A1 | 6/2008 | Loh et al. | |
| 2008/0167736 A1 | 7/2008 | Swayze | |
| 2008/0185419 A1 | 8/2008 | Smith et al. | |
| 2008/0188841 A1 | 8/2008 | Tomasello et al. | |
| 2008/0197167 A1 | 8/2008 | Viola et al. | |
| 2008/0208195 A1 | 8/2008 | Shores et al. | |
| 2008/0237296 A1 | 10/2008 | Boudreaux et al. | |
| 2008/0251561 A1 | 10/2008 | Eades et al. | |
| 2008/0255413 A1* | 10/2008 | Zemlok | A61B 17/068 600/106 |
| 2008/0255607 A1 | 10/2008 | Zemlok | |
| 2008/0262654 A1 | 10/2008 | Omori et al. | |
| 2008/0308603 A1 | 12/2008 | Shelton et al. | |
| 2009/0012533 A1 | 1/2009 | Barbagli et al. | |
| 2009/0012556 A1 | 1/2009 | Boudreaux et al. | |
| 2009/0057369 A1* | 3/2009 | Smith | A61B 17/07207 227/175.1 |
| 2009/0090763 A1 | 4/2009 | Zemlok et al. | |
| 2009/0099876 A1 | 4/2009 | Whitman | |
| 2009/0108048 A1* | 4/2009 | Zemlok | A61B 17/07207 227/175.1 |
| 2009/0138006 A1 | 5/2009 | Bales et al. | |
| 2009/0171147 A1 | 7/2009 | Lee et al. | |
| 2009/0182193 A1 | 7/2009 | Whitman et al. | |
| 2009/0209946 A1 | 8/2009 | Swayze et al. | |
| 2009/0209990 A1 | 8/2009 | Yates et al. | |
| 2009/0254094 A1 | 10/2009 | Knapp et al. | |
| 2009/0299141 A1 | 12/2009 | Downey | |
| 2010/0023022 A1 | 1/2010 | Zeiner | |
| 2010/0069942 A1 | 3/2010 | Shelton, IV | |
| 2010/0193568 A1 | 8/2010 | Scheib et al. | |
| 2010/0211053 A1 | 8/2010 | Ross et al. | |
| 2010/0225073 A1 | 9/2010 | Porter et al. | |
| 2010/0270355 A1* | 10/2010 | Whitman | A61B 17/068 227/176.1 |
| 2011/0011915 A1 | 1/2011 | Shelton, IV | |
| 2011/0024479 A1 | 2/2011 | Swensgard et al. | |
| 2011/0071508 A1 | 3/2011 | Duval et al. | |
| 2011/0077673 A1 | 3/2011 | Grubac et al. | |
| 2011/0121049 A1* | 5/2011 | Malinouskas | A61B 17/07207 227/175.1 |
| 2011/0125138 A1* | 5/2011 | Malinouskas | A61B 17/068 606/1 |
| 2011/0139851 A1 | 6/2011 | McCuen | |
| 2011/0155783 A1 | 6/2011 | Rajappa et al. | |
| 2011/0155786 A1 | 6/2011 | Shelton, IV | |
| 2011/0172648 A1 | 7/2011 | Jeong | |
| 2011/0174009 A1 | 7/2011 | Iizuka et al. | |
| 2011/0174099 A1 | 7/2011 | Ross et al. | |
| 2011/0184245 A1 | 7/2011 | Xia et al. | |
| 2011/0204119 A1 | 8/2011 | McCuen | |
| 2011/0218522 A1 | 9/2011 | Whitman | |
| 2011/0276057 A1 | 11/2011 | Conlon et al. | |
| 2011/0290854 A1 | 12/2011 | Timm et al. | |
| 2011/0295242 A1 | 12/2011 | Spivey et al. | |
| 2011/0295269 A1 | 12/2011 | Swensgard et al. | |
| 2012/0000962 A1 | 1/2012 | Racenet et al. | |
| 2012/0074199 A1 | 3/2012 | Olson et al. | |
| 2012/0089131 A1 | 4/2012 | Zemlok et al. | |
| 2012/0104071 A1 | 5/2012 | Bryant | |
| 2012/0116368 A1 | 5/2012 | Viola | |
| 2012/0143002 A1 | 6/2012 | Aranyi et al. | |
| 2012/0172924 A1 | 7/2012 | Allen, IV | |
| 2012/0211542 A1 | 8/2012 | Racenet | |
| 2012/0223121 A1 | 9/2012 | Viola et al. | |
| 2012/0245428 A1 | 9/2012 | Smith et al. | |
| 2012/0253329 A1 | 10/2012 | Zemlok et al. | |
| 2012/0310220 A1 | 12/2012 | Malkowski et al. | |
| 2012/0323226 A1 | 12/2012 | Chowaniec et al. | |
| 2012/0330285 A1 | 12/2012 | Hartoumbekis et al. | |
| 2013/0093149 A1 | 4/2013 | Saur et al. | |
| 2013/0181035 A1 | 7/2013 | Milliman | |
| 2013/0184704 A1 | 7/2013 | Beardsley et al. | |
| 2013/0214025 A1 | 8/2013 | Zemlok et al. | |
| 2013/0274722 A1 | 10/2013 | Kostrzewski et al. | |
| 2013/0282052 A1 | 10/2013 | Aranyi | |
| 2013/0292451 A1 | 11/2013 | Viola et al. | |
| 2013/0313304 A1 | 11/2013 | Shelton, IV et al. | |
| 2013/0317486 A1 | 11/2013 | Nicholas et al. | |
| 2013/0319706 A1 | 12/2013 | Nicholas et al. | |
| 2013/0324978 A1 | 12/2013 | Nicholas et al. | |
| 2013/0324979 A1 | 12/2013 | Nicholas et al. | |
| 2013/0334281 A1 | 12/2013 | Williams | |
| 2014/0012236 A1 | 1/2014 | Williams et al. | |
| 2014/0012237 A1 | 1/2014 | Pribanic et al. | |
| 2014/0012289 A1 | 1/2014 | Snow et al. | |

(56) References Cited

U.S. PATENT DOCUMENTS

| | | |
|---|---|---|
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 1957854 A | 5/2007 |
| CN | 101495046 A | 7/2009 |
| CN | 102247182 A | 11/2011 |
| DE | 102008053842 A1 | 5/2010 |
| EP | 0705571 A1 | 4/1996 |
| EP | 0834280 A1 | 4/1998 |
| EP | 1273272 A2 | 1/2003 |
| EP | 1563793 A1 | 8/2005 |
| EP | 1769754 A1 | 4/2007 |
| EP | 2316345 A1 | 5/2011 |
| EP | 2668910 A2 | 12/2013 |
| ES | 2333509 A1 | 2/2010 |
| JP | 09149906 | 6/1997 |
| JP | 2005-125075 A | 5/2005 |
| KR | 20120022521 A | 3/2012 |
| WO | 2011/108840 A2 | 9/2011 |

OTHER PUBLICATIONS

Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
European Search Report corresponding to European Application No. 10 01 2659.8, completed Dec. 21, 2010; dated Jan. 3, 2011; 3 pages.

(56) References Cited

OTHER PUBLICATIONS

European Search Report corresponding to European Application No. 10 01 2646.5, completed Feb. 11, 2011; dated Feb. 22, 2011; 3 pages.
European Search Report corresponding to European Application No. 12 19 0101, dated Feb. 12, 2015; 9 pages.
Chinese Office Action dated Dec. 17, 2015, issued in Chinese Application No. 201210418425.
Australian Examination Report 1 dated Aug. 28, 2013, issued in Australian Application No. 2012238268.
Australian Examination Report 2 dated Oct. 8, 2014, issued in Australian Application No. 2012238268.
European Communication for Application No. 12 190 101.1 dated Sep. 26, 2019.

* cited by examiner

SYSTEM AND METHOD OF USING SIMULATION RELOAD TO OPTIMIZE STAPLE FORMATION

CROSS REFERENCE TO RELATED APPLICATION

The present application is a divisional of U.S. patent application Ser. No. 13/633,213, filed Oct. 2, 2012, which claims the benefit of and priority to U.S. Provisional Patent Application Ser. No. 61/551,956, filed Oct. 27, 2011, the entire contents of each of which are incorporated herein by reference.

BACKGROUND

Technical Field

The present disclosure relates generally to medical devices. More specifically, the present disclosure relates generally to systems and methods for controlled tissue compression.

Background of the Related Art

Some surgical procedures require the compression, e.g., clamping, of a patient's tissue. Such procedures may include, e.g., anastomosing, stapling, and resecting of tissue. For example, where cancerous tissue is identified in a patient's gastrointestinal tract, the cancerous tissue may need to be surgically removed. Where, for example, the cancerous tissue is located on the colon and is accessible by surgical instrumentation, the surgeon may make an incision in the patient's abdomen to allow access to the bowel. The surgeon may then use a linear cutting and stapling device, such as that described in U.S. patent application Ser. No. 12/235,362, filed on Sep. 22, 2008, which is expressly incorporated herein in its entirety by reference, to cut and staple the colon tissue on opposite sides of the cancerous portion to be removed. In this procedure, the colon is externally clamped (e.g., between opposed jaws) to compress the tissue. While the tissue is compressed, a cutter and a stapler are activated to make a linear cut and apply typically two linear rows of staples in the areas adjacent the cut. The stapling thus closes both open ends of the portion of the bowel to be removed, as well as providing a temporary closure of the two cut ends of the bowel. This closure limits exposure of the surrounding tissue to the interior of the bowel, thus limiting the risk of infection. After the cutting and stapling procedure, the cancerous portion of tissue may be removed from the patient's body.

After the resection of the cancerous tissue, the surgeon may employ an anastomosing and stapling device, e.g., a circular stapler/cutter. During this procedure, a head portion is positioned within the colon adjacent one of the cut ends and a base or shaft portion is positioned within the colon adjacent the other cut end. The head portion and the base portion may be coupled via a shaft and/or cable that extends out of one cut end and into the other. Via this coupling, the surgeon is able to actuate the anastomosing and stapling device to draw the head portion and the base portion together. After the two cut ends of the colon contact each other, the actuation continues such that the two portions of the colon are clamped together at an annular area of contact. While clamped, the anastomosing and stapling device may be further actuated to apply an annular ring of staples into the compressed tissue. The device may also cut excess tissue disposed within the colon. The head portion and the base portion are then moved apart and the anastomosing and stapling device removed from the patient.

To achieve effective stapling in the above procedures, the tissue must be compressed to the extent that there is an adequately small tissue gap, e.g., one millimeter, between the faces of the tool. If the clamping structures of the instrument are exposed to enough force, maintaining a uniform target tissue gap across the length of tissue to be stapled may be difficult or even impossible. For example, where the clamping structures are cantilevered jaws of a linear stapler, the distal portion of the jaws may splay outwardly from each other under high clamping forces. Where one or both of the jaws splay in this manner, the tissue gap typically increases toward the distal ends of the jaws. Where this tissue gap exceeds an acceptable range, staples may not adequately close the tissue to prevent contamination. This may result from, e.g., the initial stapled gap being too large and/or failure of the staple (e.g., separation from one or more of the portions of stapled tissue) due to improper formation resulting from, e.g., too large a gap between a staple pusher and an anvil that closes the staple.

Powered stapling devices may use control systems and algorithms to control a driving motor in order to properly clamp tissue and achieve a desired tissue gap. Many of these algorithms use standard variables that are based on type of tissue being clamped, type of disease affecting the tissue, the stage of the disease, etc along with typical characteristics of the stapling device itself. However, because each stapling device is different due to motor variation, device construction, wear, mechanical tolerances and mechanical play etc., the variables used in one stapling device to achieve a desired tissue gap may not be effective in a different stapling device of the same type. There is a need to calibrate powered stapling devices and provide inputs to the device control systems in order to improve optimum tissue gaps and staple formation while stapling.

SUMMARY

In an embodiment of the present disclosure a system and method for testing a powered surgical instrument is provided. The powered surgical instrument includes a processor configured to control operation of the powered surgical instrument, a memory configured to store a tissue compression program, a reload configured to clamp tissue, a motor configured to control the reload to apply a compressive force to the tissue by the reload, and at least one sensor configured to measure a current draw on the motor. The processor executes a simulation program to measure the current draw on the motor through a nominal thickness firing and the measured current draw is used to adjust the tissue compression program.

The tissue compression program includes programming code coefficients and the processor adjusts the programming code coefficients based on the measured current draw. The processor may compare the measured current draw to a predetermined current draw associated with the nominal thickness firing. The difference between the measured current draw and the predetermined current draw is used to adjust the programming code coefficients.

In another embodiment of the present disclosure, a simulation reload is provided that is configured to be coupled to a powered surgical instrument. The simulation reload may be factory calibrated and have known mechanical parameters of greater accuracy than actual reloads. The simulation reload may include a memory configured to store calibration parameters of the reload. The simulation reload may also include a memory configured to store a simulation program, a processor configured to execute the simulation program, and at least one sensor configured to measure a current draw on the motor of the powered surgical instrument. The processor executes the simulation program to measure the current draw on the motor through a nominal thickness firing and the measured current draw is stored in the memory. While the simulation program, processor and sensor are described as resident in the simulation.

In yet another embodiment of the present disclosure, a simulation system is provided. The simulation system includes a powered surgical instrument, a simulation reload, and a test platform. The powered surgical instrument includes a processor configured to control operation of the powered surgical instrument, a memory configured to store a tissue compression program, and a motor configured to control a reload to apply a compressive force to the tissue by the reload. The simulation system includes a memory configured to store a simulation program, a processor configured to execute the simulation program, and at least one sensor configured to measure a current draw on the motor of the powered surgical instrument. The simulation reload processor executes the simulation program to measure the current draw on the motor through a nominal thickness firing and the measured current draw is stored in the memory of the simulation reload. The test platform includes a first interface configured to be operatively connected to the powered surgical instrument and a second interface configured to be operatively connected to the simulation reload. The test platform is configured to adjust the tissue compression program stored in the memory of the powered surgical instrument based on the measured current draw stored in the memory of the simulation reload. While the simulation program, processor and sensor are described as resident in the simulation reload in one embodiment, these components may be located in any portion of the system provided with the provision of suitable data transmission between the components.

The tissue compression program includes programming code coefficients and the test platform adjusts the programming code coefficients based on the measured current draw. The test platform may compare the measured current draw to a predetermined current draw associated with the nominal thickness firing. The difference between the measured current draw and the predetermined current draw is used to adjust the programming code coefficients.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1A:
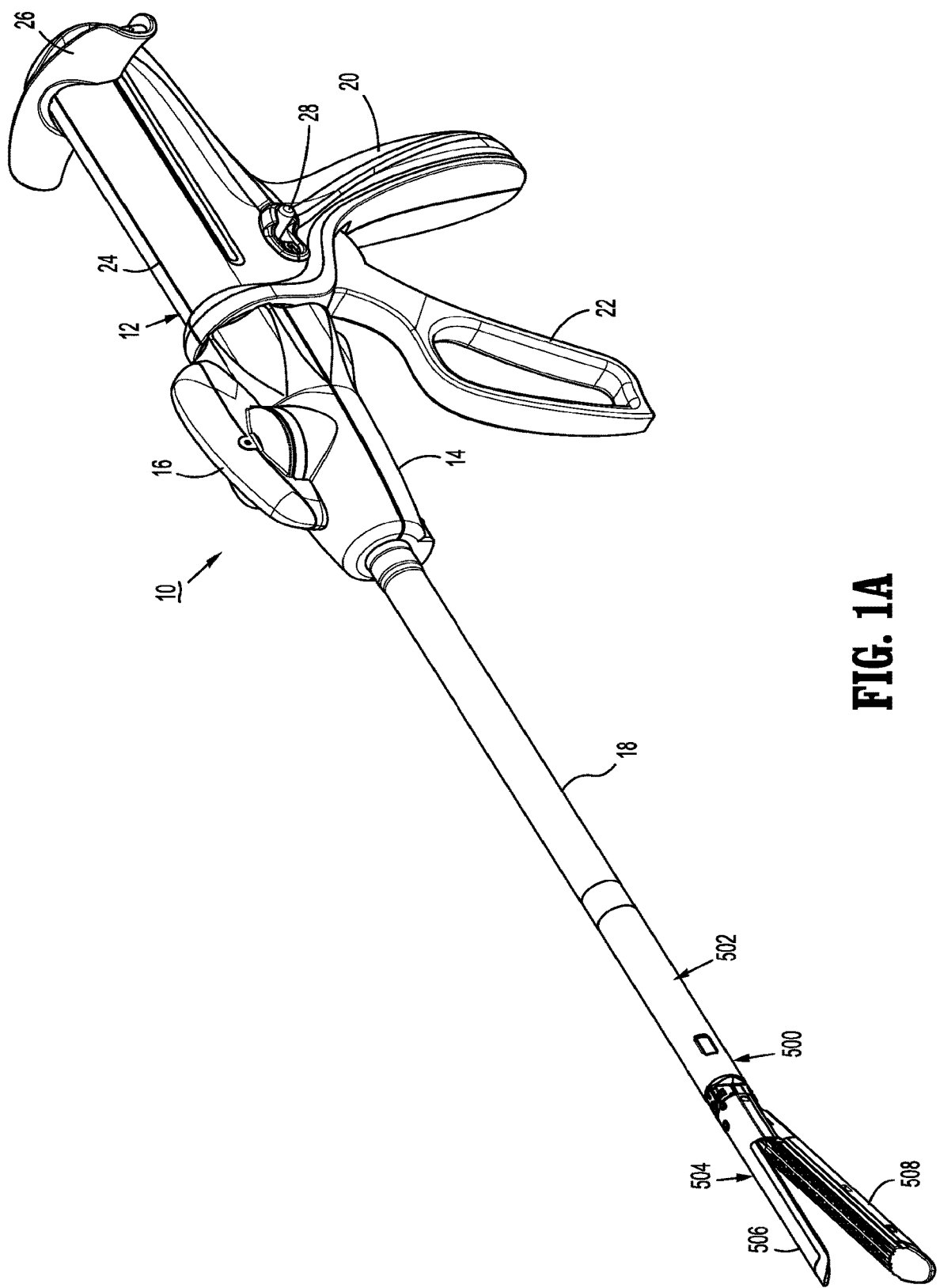
FIGS. 1A-1C are perspective views of powered surgical instruments according to embodiments of the present disclosure.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the user and the term "distal" refers to the end of the apparatus which is farther away from the user. The term "clinician" refers to any medical professional (i.e., doctor, surgeon, nurse, or the like) performing a medical procedure involving the use of embodiments described herein.

As seen in FIG. 1A, powered surgical instrument, e.g., a surgical stapler, in accordance with the present disclosure is referred to as reference numeral 10. Powered surgical instrument 10 is merely an example of a surgical instrument that utilizes the embodiments of the present disclosure described herein. With reference to FIG. 1A, powered surgical instrument 10 includes a handle assembly 12, a rotation knob 14, an articulation lever 16, an elongated body portion 18 and a reload 500. Handle assembly 12 includes a stationary handle portion 20, a movable handle portion or trigger 22, a barrel portion 24, and retraction knobs 26. An actuator button 28 extends transversely through and projects outwardly from opposite sides of handle assembly 12.

Reload 500 includes a proximal body portion 502 and a tool assembly 504. Proximal body portion 502 is releasably attached to a distal end of elongated body portion 18 and tool assembly 504 is pivotably attached to a distal end of proximal body portion 502. Tool assembly 504 includes an anvil assembly 506 and a cartridge assembly 508. Cartridge assembly 508 is pivotal in relation to anvil assembly 506 from an open or unclamped position to a closed or clamped position.

Figure 1B:
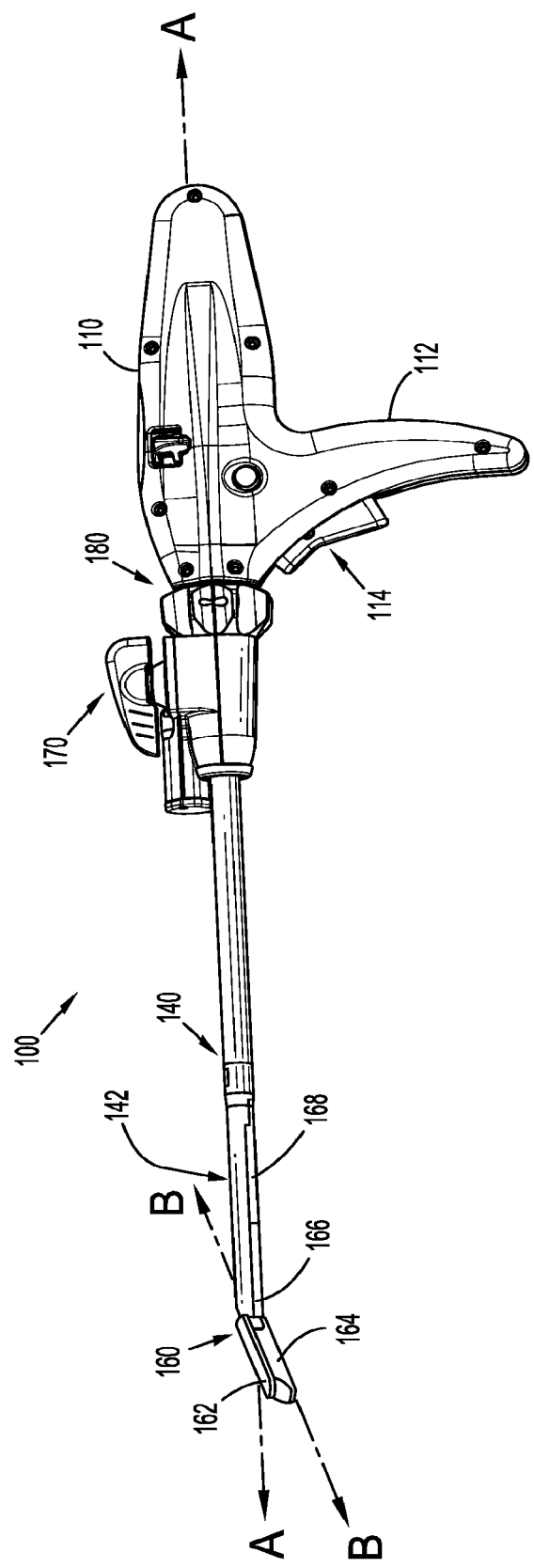

As seen in FIG. 1B, another powered surgical instrument, e.g., a surgical stapler, in accordance with the present disclosure is referred to in the figures as reference numeral 100. With reference to FIG. 1B, powered surgical instrument 100 includes a housing 110, an endoscopic portion 140 defining a first longitudinal axis A-A extending therethrough, and an end effector 160, defining a second longitudinal axis B-B extending therethrough. Endoscopic portion 140 extends distally from housing 110 and end effector 160 is disposed adjacent a distal portion 142 of endoscopic portion 140. Housing 110 includes a handle portion 112 having at least one switch 114 thereon.

Powered surgical instrument 100 also includes an articulation mechanism 170. Actuation of articulation mechanism 170 causes end effector 160 to move from its first position, where longitudinal axis B-B is substantially aligned with longitudinal axis A-A, towards a position in which longitudinal axis B-B is disposed at an angle to longitudinal axis A-A. A plurality of articulated positions is achieved. Articulation mechanism 170 is mounted to a rotating housing assembly 180.

End effector 160 includes a cartridge assembly (e.g., jaw member 164) and an anvil assembly (e.g., jaw member 162) including an anvil portion for forming the surgical fasteners when deployed from the cartridge assembly. Cartridge assembly 164 has a cartridge body that houses a plurality of staples. At least one of anvil assembly 162 and cartridge assembly 164 is movable in relation to one another between an open position where anvil assembly 162 is spaced from cartridge assembly 164 and an approximated position for clamping tissue where anvil assembly 162 is in juxtaposed alignment with cartridge assembly 164. In an embodiment, the staples housed in cartridge assembly 164 are arranged to apply linear rows of staples to body tissue.

It is further envisioned that end effector 160 is attached to a mounting portion 166, which is pivotably attached to a body portion 168. Body portion 168 may be integral with endoscopic portion 140 of powered surgical instrument 100, or may be removably attached thereto to provide a replaceable, disposable loading unit (DLU) or single use loading unit (SULU). The loading unit may be connectable to endoscopic portion 140 through a bayonet connection or other suitable quick connect features. It is envisioned that the loading unit has an articulation link connected to mounting portion 166 of the loading unit and the articulation link is connected to a linkage rod so that the end effector 160 is articulated as the linkage rod is translated in the distal-proximal direction along first longitudinal axis A-A. Other means of connecting end effector 160 to endoscopic portion 140 to allow articulation may be used. For example, a flexible tube or a plurality of pivotable members may be used. Alternatively, the cartridge assembly or a portion thereof may be replaceable or removable.

A loading unit may incorporate (or be configured to incorporate) various end effectors, such as vessel sealing devices, linear stapling devices, circular stapling devices, cutters, etc. Such end effectors may be coupled to endoscopic portion 140 of powered surgical instrument 100. An intermediate flexible shaft may be included between handle portion 112 and loading unit. An example of a flexible shaft is described in detail in commonly-owned U.S. patent application Ser. No. 11/786,934, entitled "Powered Surgical Instrument", filed on Apr. 13, 2007, the contents of which are hereby incorporated by reference in their entirety.

Further details of powered surgical instrument 100 are described in detail in commonly-owned U.S. patent application Ser. No. 11/724,733 entitled "Surgical Stapling Apparatus with Powered Articulation", filed on Mar. 15, 2007, now U.S. Pat. No. 7,431,188, the contents of which are hereby incorporated by reference in their entirety.

Figure 1C:
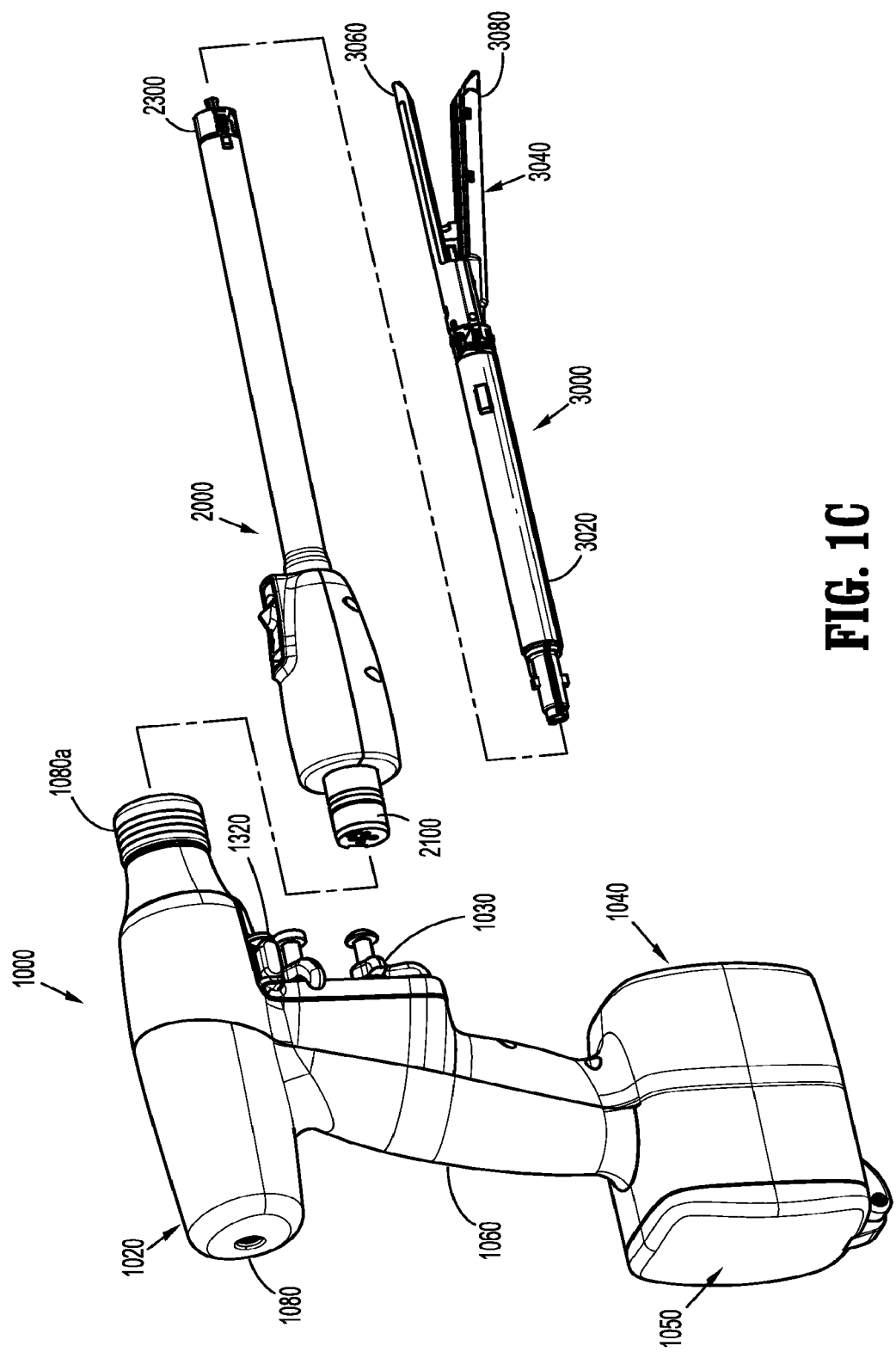

As seen in FIG. 1C, another powered surgical instrument, e.g., a surgical stapler, in accordance with the present disclosure is referred to in the figures as reference numeral 1000. With reference to FIG. 113, powered surgical instrument 1000 includes a handle housing 1020 having a lower housing portion 1040, an intermediate housing portion 106 extending from and/or supported on lower housing portion 1004, and an upper housing portion 1080 extending from and/or supported on intermediate housing portion 1060.

Upper housing portion 1080 defines a connecting portion 1080a configured to accept a corresponding drive coupling assembly 2100 of adapter 2000.

As seen in FIG. 1C, powered surgical instrument 1000 includes a fire button or safety switch 1320 supported between intermediate housing portion 1060 and upper housing portion 1080, and situated above trigger housing 1030. In use, tool assembly 3040 is actuated between opened and closed conditions as needed and/or desired. Powered surgical instrument 1000 is configured to move anvil assembly 3060 relative to cartridge assembly 3080 of reload 3000, and/or to fire a stapling and cutting cartridge within cartridge assembly 3080 of reload 3000.

In order to fire reload 3000, to expel fasteners therefrom when tool assembly 3040 of reload 3000 is in a closed condition, safety switch 1320 is depressed thereby instructing powered surgical instrument 1000 that reload 3000 is ready to expel fasteners therefrom.

Figure 2:
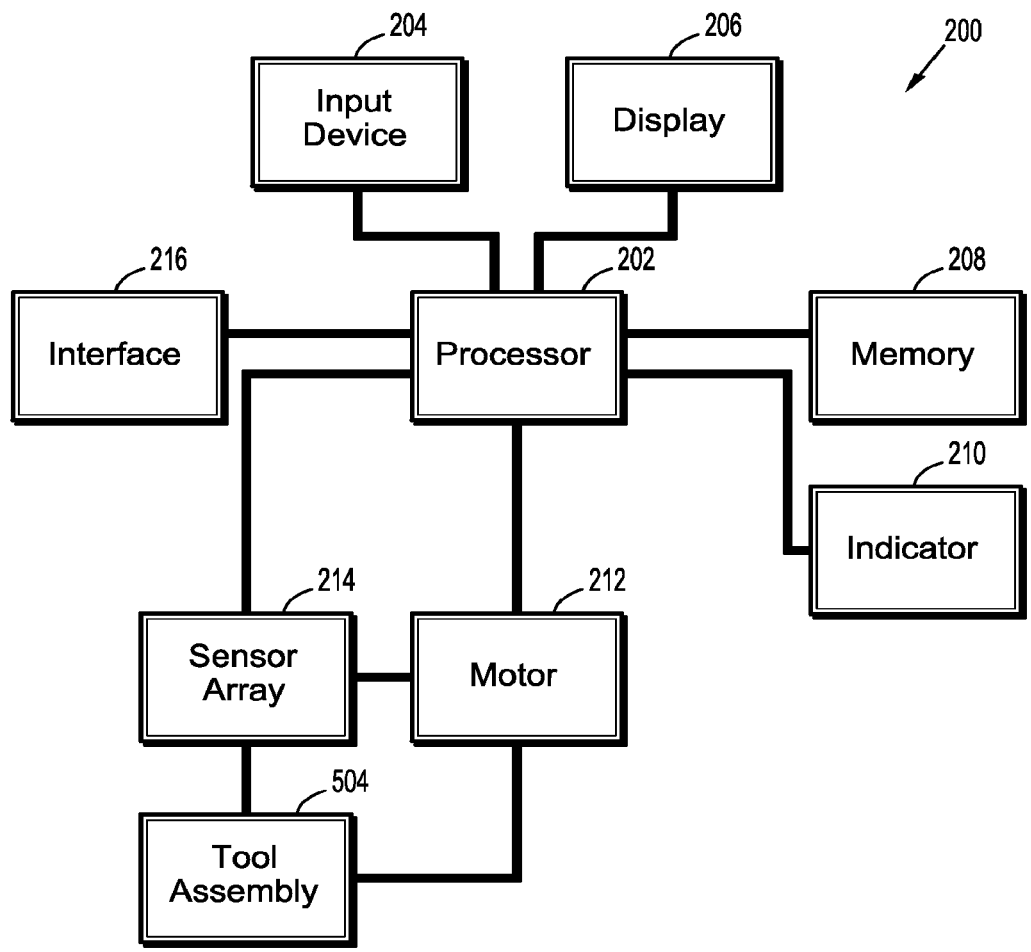
FIG. 2 is a system block diagram of a powered surgical instrument according to an embodiment of the present disclosure.

As seen in FIG. 2, powered surgical instrument 10, 100, and 1000 may include a control system designated generally as 200 in FIG. 2. Control system 200 may be integrated in any of the handle assemblies described above or some of the components may be provided in a stand-alone unit. Control system 200 includes a processor 202, an input device 204, a display 206, a memory 208, an indicator 210, a motor 212 and a sensor array 214.

Processor 202 may be an integrated circuit or may include analog and/or logic circuitry that may be used to: execute instructions according to inputs provided by the input device 204 or sensor array 214, execute instructions according to a program provided in memory 208; and/or control motor 212 to thereby control the tool assembly 504 to perform any number of functions, including and not limited to clamping tissue therebetween.

Input device 204 may include a keyboard, a touch-screen input device, switches and/or buttons to control operation of the powered surgical instrument 10. Input device 204 may be used to: select between tissue management modes; control tool assembly 504; apply a staple or clamp; and input tissue properties such as tissue type and/or disease.

Display 206 may include a liquid crystal display, a light-emitting diode (LED) display or the like. Display 206 may output a status of the powered surgical instrument, measured tissue properties, number of staples/clips applied, etc.

Control system 200 may also include an indicator 210 that may include at least one light emitting diode (LED) to indicate whether a tissue gap range, between anvil assembly 506 and cartridge assembly 508 of tool assembly 504, has been met.

Sensor array 214 determines tissue properties by detecting the current draw on motor 212 or a dwell effect at tool assembly 504. The detected tissue properties are used to determine the tissue management mode, tissue gap range, firing parameters, motor speed, modulation/pulse of the signal applied to the motor, deployment or non-deployment of staple/clips, etc. The detected tissue properties are used as an input to an iterative adjustment of the clamping pressure and a duration for a tissue management mode.

Memory 208 may be a volatile type memory (e.g., random access memory (RAM)) and/or non-volatile type memory (e.g., flash media, disk media, etc.) that stores programs or sets of instructions for the operation of the powered surgical instrument 10. Such programs include a number of tissue management modes that perform a controlled tissue compression (CTC) operation that may be used to clamp tissue in order to apply a staple or clip to the tissue grasped by tool assembly 504. Memory 208 may also store correlation tables to correlate tissue type and disease type to the requisite tissue gap range and firing parameters that need to be achieved to successfully apply a staple or clip to tissue.

Control system 200 may also include an interface 216 that may be removably coupled to a simulation reload 300 or test platform 400, that will be described hereinbelow. Processor 202 may transmit and/or receive data to simulation reload 300 or test platform 400 through interface 216. In addition, memory 208 may transmit and/or receive data to simulation reload 300 or test platform 400 via interface 216.

During a controlled tissue compression (CTC) operation, motor 212 controls tool assembly 504 to apply a compressive force to tissue grasped between anvil assembly 506 and cartridge assembly 508 of tool assembly 504. Control of motor 212 is based on a CTC program stored in memory 208. Depending on the type of tissue and/or disease type, processor 202 executes the CTC program stored in memory 208. Processor 202 calculates the requisite tissue gap and the firing parameters based on programming code coefficients stored in memory 208 and transmits a signal to motor 212 based on the calculated requisite tissue gap and firing parameters. Motor 212 then controls tool assembly 504 to provide the appropriate tissue compression to achieve an optimal staple formation.

Memory 208 may have a simulation program stored therein to adjust the programming code coefficients used to calculate the firing parameters of instrument 10. Once powered surgical instrument 10 is assembled, powered surgical instrument 10 may be placed in a reload simulation state by processor 202. Powered surgical instrument 10 is fired through a nominal thickness and sensor array 214 measures the current draw on the motor 212. The measured current draw is transmitted to processor 202 which then compares the measured current draw for the simulation state to a predetermined current draw value stored in memory 208 that corresponds to the nominal thickness. Based on the difference between the measured current draw for the simulation state and the predetermined current draw stored in memory 208, processor 202 adjusts the programming code coefficients for the particular powered surgical instrument 10.

Figure 3:
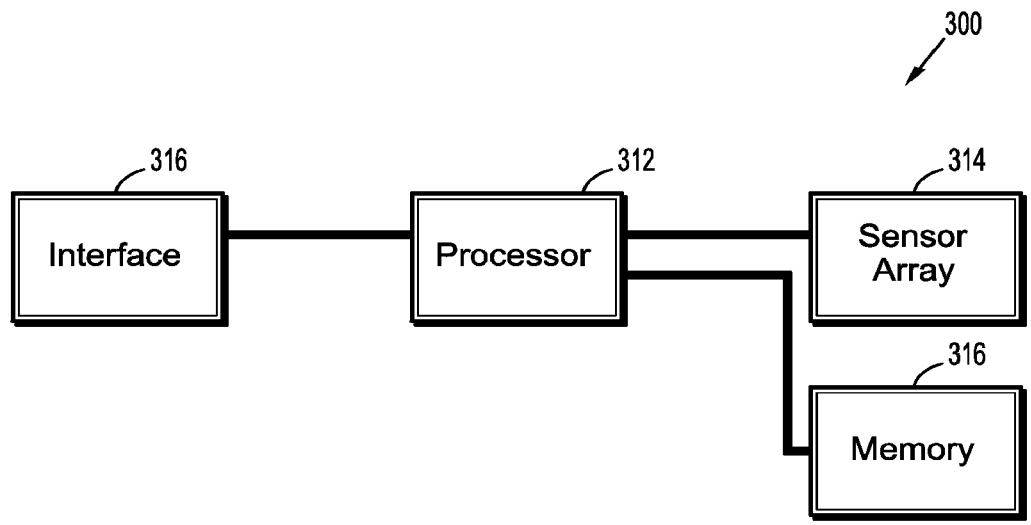
FIG. 3 is a system block diagram of a simulation reload according to an embodiment of the present disclosure.

FIG. 3 depicts a simulation reload 300 in accordance with an embodiment of the present disclosure. After a powered surgical instrument 10 is assembled, instrument 10 is tested using a simulation reload 300 in place of an actual reload 500. Simulation reload 300 is similar to reload 500 and may further include a processor 312, a sensor array 314, and a memory 316. Processor 312 may be an integrated circuit or may include analog and/or logic circuitry that may be used to execute instructions according to inputs provided by sensor array 314 and/or execute instructions according to a program provided in memory 316. Sensor array 314 determines tissue properties by detecting the current draw on motor 212 or a dwell effect at tool assembly 504. Memory 208 may be a volatile type memory (e.g., random access memory (RAM)) and/or non-volatile type memory (e.g., flash media, disk media, etc.) that stores readings from sensor array 314.

Simulation reload 300 may also include an interface 316 that may be removably coupled to interface 216 of control system 200 or irremovably coupled to a test platform 400. Interface 316 may transmit sensor readings from sensor array 314 and/or memory 316 to processor 202 of control system 200.

Simulation reload 300 is loaded into powered surgical instrument 10 to test instrument 10 through a predetermined nominal thickness firing. Sensor array 314 measures the current draw on motor 212 when the powered surgical instrument 10 is used to grasp tissue and simulate a staple firing and stores the measured current draw in memory 216 and/or 316. The measured current draw may be transmitted to processor 202 to adjust the firing parameters for the tested powered surgical instrument 10.

In another embodiment, simulation reload 300 may transmit measurements from sensor array 314 directly to processor 202 via interface 316, or sensor array 214 in control system 200 may be used to measure the current draw on the motor.

Figure 4:
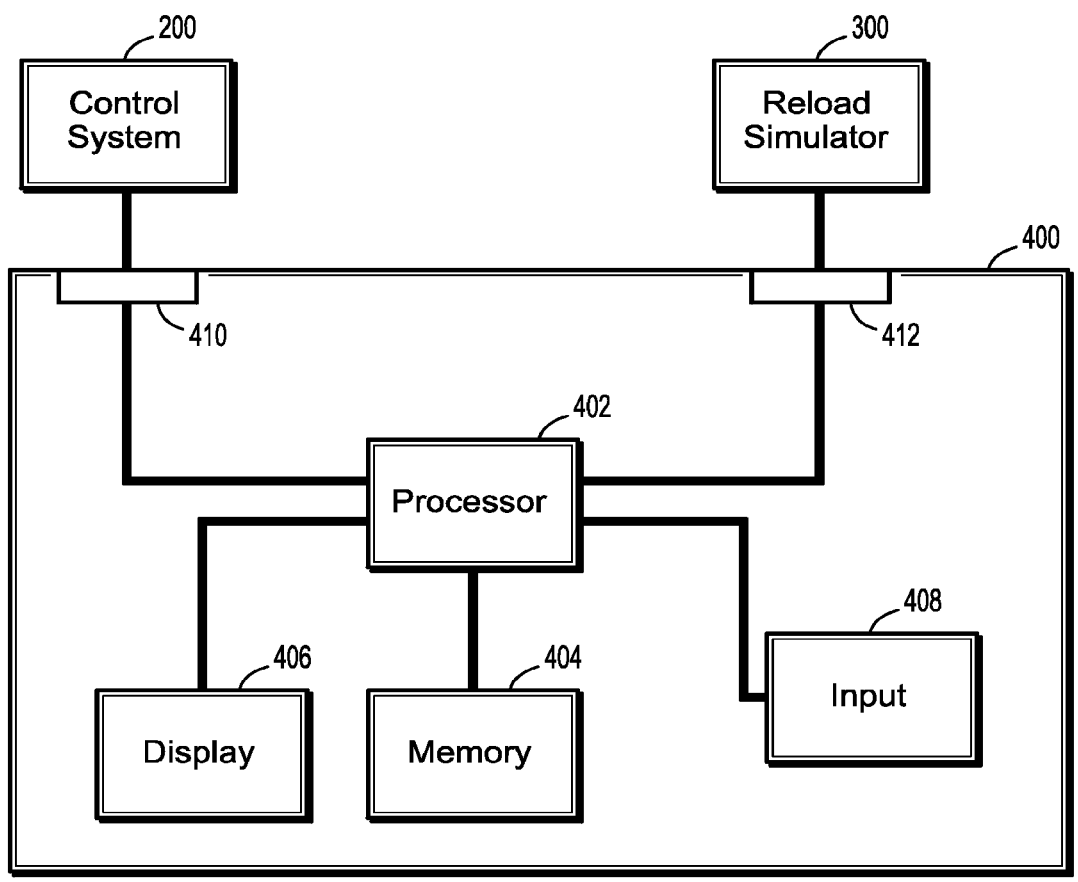
FIG. 4 is a system block diagram of a programming device according to an embodiment of the present disclosure.

FIG. 4 depicts a system block diagram for a test platform 400 according to another embodiment of the present disclosure. As shown in FIG. 4, test platform 400 includes a processor 402, a memory 404, a display 406, an input device 408, an interface 410, and an interface 412.

Processor 402 may be an integrated circuit or may include analog and/or logic circuitry that may be used to: execute instructions according to inputs provided by the input device 408 and/or execute instructions according to a program provided in memory 404. Input device 408 may include a keyboard, a touch-screen input device, switches and/or buttons to control operation of test platform 400. Display 406 may include a liquid crystal display, a light emitting diode display or the like. Memory 404 may be a volatile type memory (e.g., random access memory (RAM)) and/or non-volatile type memory (e.g., flash media, disk media, etc.) that stores programs or sets of instructions for the operation of test platform 400.

After simulation reload 300 is used to test powered surgical instrument 10, simulation reload 300 and powered surgical instrument 10 are removably coupled to first and second interfaces 410 and 412, respectively. The measured current draw stored in simulation reload 300 is downloaded to test platform 400 and stored in memory 404. Using display 406, an operator can see the results of the test firing performed on powered surgical instrument 10 and, using input device 408, reprogram powered surgical instrument 10 to compensate for the individual characteristics of powered surgical instrument 10, e.g., motor variation, friction, manufacturing tolerances, etc.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. A powered surgical instrument comprising:
   a processor configured to control operation of the powered surgical instrument;
   a memory configured to store a tissue compression program;
   a motor configured to control a reload to apply a compressive force to tissue by the reload; and
   at least one sensor configured to measure a current draw on the motor,
   wherein, when the powered surgical instrument is placed in a reload simulation state to test the powered surgical instrument, the processor executes a simulation program to measure the current draw on the motor during the simulation state when the powered surgical instrument simulates a staple firing through a predetermined nominal thickness; and
   wherein the measured current draw on the motor during the simulation state is used to adjust the tissue compression program.

2. The powered surgical instrument of claim 1, wherein the tissue compression program includes programming code coefficients, and wherein the processor adjusts the programming code coefficients based on the measured current draw on the motor during the simulation state.

3. The powered surgical instrument of claim 2, wherein the processor compares the measured current draw on the motor during the simulation state to a predetermined current draw associated with the predetermined nominal thickness firing.

4. The powered surgical instrument of claim 3, wherein the difference between the measured current draw on the motor during the simulation state and the predetermined current draw is used to adjust the programming code coefficients.

5. The powered surgical instrument of claim 2, wherein the programming code coefficients are linear coefficients.

6. The powered surgical instrument of claim 1, wherein when the powered surgical instrument is placed in a non-simulation state, and wherein during a controlled tissue compression the motor is controlled based on the adjusted tissue compression program.

7. The powered surgical instrument of claim 6, wherein when the powered surgical instrument is placed in a non-simulation state, based on a tissue type, the processor calculates a tissue gap and a firing parameter based on an adjusted programming code coefficient and transmits a signal to the motor based on the calculated tissue gap and firing parameter.

8. The powered surgical instrument of claim 1, wherein the powered surgical instrument is switched from the reload simulation state to the non-simulation state to perform a controlled tissue compression based on the adjusted tissue compression program.

9. A simulation reload coupled to a powered surgical instrument having a motor, the simulation reload comprising:
    a memory that stores a simulation program; and
    a processor that executes the simulation program,
    wherein the processor executes the simulation program to measure a current draw on the motor during the simulation state through a predetermined nominal thickness to test the powered surgical instrument,
    wherein the measured current draw on the motor during the simulation state is stored in the memory, and
    wherein measured current draw on the motor during the simulation state is used to adjust a tissue compression program stored in the powered surgical instrument.

* * * * *